(12) United States Patent
Hsu

(10) Patent No.: US 8,038,859 B2
(45) Date of Patent: Oct. 18, 2011

(54) ELECTROCHEMICAL SENSOR AND METHOD FOR ANALYZING LIQUID SAMPLE

(75) Inventor: Tien-Tsai Hsu, Hsinchu (TW)

(73) Assignee: HMD Biomedical Inc., Hsin-Chu (TW)

( * ) Notice: Subject to any disclaimer, the term of this patent is extended or adjusted under 35 U.S.C. 154(b) by 995 days.

(21) Appl. No.: 11/413,179

(22) Filed: Apr. 28, 2006

(65) Prior Publication Data

US 2007/0251836 A1    Nov. 1, 2007

(51) Int. Cl.
*G01N 27/327* (2006.01)
(52) U.S. Cl. .................................. 204/403.01; 205/792
(58) Field of Classification Search .......... 204/411–412, 204/403.04, 403.09–403.11; 205/77.5, 778, 205/792; 436/62–71, 500–548; 422/68.1–98; 435/4–40.52
See application file for complete search history.

(56) References Cited

U.S. PATENT DOCUMENTS

| | | | |
|---|---|---|---|
| 5,352,351 A | 10/1994 | White et al. | |
| 5,611,909 A | 3/1997 | Studer | |
| 5,650,062 A * | 7/1997 | Ikeda et al. | 205/778 |
| 5,653,863 A | 8/1997 | Genshaw et al. | |
| 6,299,757 B1 | 10/2001 | Feldman et al. | |
| 6,338,790 B1 * | 1/2002 | Feldman et al. | 205/777.5 |
| 6,531,040 B2 | 3/2003 | Musho et al. | |
| 6,576,117 B1 | 6/2003 | Iketaki et al. | |
| 2001/0042683 A1 | 11/2001 | Musho et al. | |
| 2004/0011672 A1 * | 1/2004 | Ohara et al. | 205/792 |
| 2004/0045821 A1 * | 3/2004 | Cui et al. | 204/403.02 |
| 2004/0200720 A1 | 10/2004 | Musho et al. | |
| 2004/0222092 A1 | 11/2004 | Musho et al. | |
| 2005/0004226 A1 | 1/2005 | Lu et al. | |

FOREIGN PATENT DOCUMENTS

| | | |
|---|---|---|
| EP | 1074832 A1 | 2/2001 |
| EP | 1081490 A1 | 3/2001 |
| GB | 2296332 A | 6/1996 |
| WO | 2005078437 A1 | 8/2005 |

OTHER PUBLICATIONS

International Search Report mailed Aug. 6, 2005 in PCT/US2005/004226 (3 pages).

* cited by examiner

*Primary Examiner* — Alex Noguerola
*Assistant Examiner* — Gurpreet Kaur

(57) ABSTRACT

An electrochemical sensor for analyzing a liquid sample, which is adapted to be connected with an electrochemical meter, comprises a channel for delivering the liquid sample; and a first conducting portion and a second conducting portion separated and exposed in the channel; wherein the first conducting portion generates a first pulse signal when it is contacted by the liquid sample, and the second conducting portion generates a second pulse signal when it is contacted by the liquid sample. The electrochemical meter obtains viscosity of the liquid sample according to a time difference between the first and second pulse signals.

4 Claims, 4 Drawing Sheets

ELECTROCHEMICAL SENSOR AND METHOD FOR ANALYZING LIQUID SAMPLE

BACKGROUND OF THE INVENTION

1. Field of the Invention

This invention generally relates to an electrochemical sensor for analyzing a liquid sample, and more particularly to an electrochemical sensor capable of measuring viscosity of a liquid sample.

2. Description of the Related Art

Electrochemical biosensors have been widely used to determine the concentrations of various analytes in liquid samples, e.g. blood and urine. There are already various electrochemical biosensors, e.g. blood glucose biosensors, cholesterol biosensors, uric acid biosensors and lactic acid biosensors, on the market. In particular, blood glucose biosensors are in widespread use and have become daily necessities for diabetics. Generally, a blood glucose biosensor is formed in a strip shape and uses at least two electrodes, e.g. a working electrode and a counter electrode, for generating an electrical signal, which is proportional to the amount of glucose in a blood sample, and transmitting the electrical signal to a blood glucose meter for showing the blood glucose level.

In recent years, there are many companies, e.g. Roche, LifeScan (Johnson & Johnson), Bayer, TheraSense and MediSense (Abbott), producing blood glucose biosensors and meters such as Roche's Accu-Chek, which is the largest market share, LifeScan's OneTouch, TheraSense's FreeStyle and MediSense's Precision. These products require only a blood sample of less than 3 microliters and take only around five to fifteen seconds to show a reading corresponding to the glucose level in the blood sample. However, none of these products can measure viscosity of a blood sample.

In many researches and clinical practices, it has been presented that many diseases such as high blood pressure, heart attack, coronary heart disease, myocardial infarction, diabetes, malignancy, and chronic hepatitis, etc., are all related to elevated blood viscosity. Accordingly, blood viscosity has become an important index for monitoring disease progression.

In the prior art, blood viscosity can be measured by a blood diluting pipette. However, the blood diluting pipette generally requires a blood sample of at least 1 cc or even more and takes at least six minutes or even more to obtain the viscosity of blood. Further, this blood sample of at least 1 cc can only be obtained from a patient, for example, using a needle and syringe to obtain a useful sample volume. Therefore, these procedures are inconvenient and often painful for the patient, particularly, when frequent samples are required.

In addition, various viscometers can be commercially obtained from the market. However, these viscometers still require at least a liquid sample of several hundred microliters or even more to obtain the viscosity.

Accordingly, the present invention provides an electrochemical sensor capable of measuring viscosity of a liquid sample with a small sample volume.

SUMMARY OF THE INVENTION

It is an object of the present invention to provide an electrochemical sensor for analyzing a liquid sample, wherein the electrochemical sensor is capable of measuring viscosity of the liquid sample with a small sample volume.

It is another object of the present invention to provide an electrochemical sensing device for analyzing a liquid sample, wherein the electrochemical sensing device is capable of measuring concentration of an analyte in the liquid sample and calibrating the measured concentration of the analyte.

It is another object of the present invention to provide a method for analyzing a liquid sample, wherein the method can be applied to an electrochemical sensing device such that the electrochemical sensing device can measure not only the concentration of an analyte in the liquid sample but also the viscosity of the liquid sample.

In order to achieve the above objects, the present invention provides an electrochemical sensor for analyzing a liquid sample, which comprises a first insulating layer, a second insulating layer, a channel, a timing electrode and a counter electrode. The channel is defined between the first insulating layer and the second insulating layer for delivering the liquid sample; the timing electrode is disposed on the first insulating layer and has a first conducting portion and a second conducting portion separated and exposed in the channel; and the counter electrode is disposed on the first insulating layer and has at least one conducting portion exposed in the channel; wherein the timing electrode generates a first pulse signal to be transmitted to an electrochemical meter when the liquid sample contacts both the conducting portion of the counter electrode and the first conducting portion of the timing electrode, and generates a second pulse signal to be transmitted to the electrochemical meter when the liquid sample contacts both the conducting portion of the counter electrode and the second conducting portion of the timing electrode.

The present invention also provides an electrochemical sensing device for analyzing a liquid sample, which comprises an electrochemical meter and an electrochemical sensor electrically connected with the electrochemical meter. The electrochemical sensor has a channel for delivering the liquid sample, and a first conducting portion and a second conducting portion separated and exposed in the channel; wherein the first conducting portion generates a first pulse signal when it is contacted by the liquid sample, and the second conducting portion generates a second pulse signal when it is contacted by the liquid sample. The electrochemical meter obtains viscosity of the liquid sample according to a time difference between the first and second pulse signals.

The present invention also provides a method for analyzing a liquid sample, which is applied to an electrochemical sensing device having an electrochemical meter and an electrochemical sensor. The method of the present invention comprises disposing a first conducting portion and a second conducting portion in the electrochemical sensor; generating a first pulse signal to be transmitted to the electrochemical meter when the liquid sample contacting the first conducting portion, and generating a second pulse signal to be transmitted to the electrochemical meter when the liquid sample contacting the second conducting portion; calculating a time difference between the first pulse signal and the second pulse signal; and obtaining viscosity of said liquid sample according to said time difference. In one embodiment of the present invention, the method also comprises showing a reading corresponding to the viscosity of the liquid sample on the electrochemical meter. In another embodiment of the present invention, the method also comprises calculating and obtaining concentration of an analyte in the liquid sample according to an analyte-responsive signal; calibrating the obtained concentration of the analyte according to the time difference; and showing a reading corresponding to the calibrated concentration of the analyte on the electrochemical meter.

BRIEF DESCRIPTION OF THE DRAWINGS

Other objects, advantages, and novel features of the present invention will become more apparent from the following detailed description when taken in conjunction with the accompanying drawings.

DETAILED DESCRIPTION OF THE PREFERRED EMBODIMENT

Figure 1:
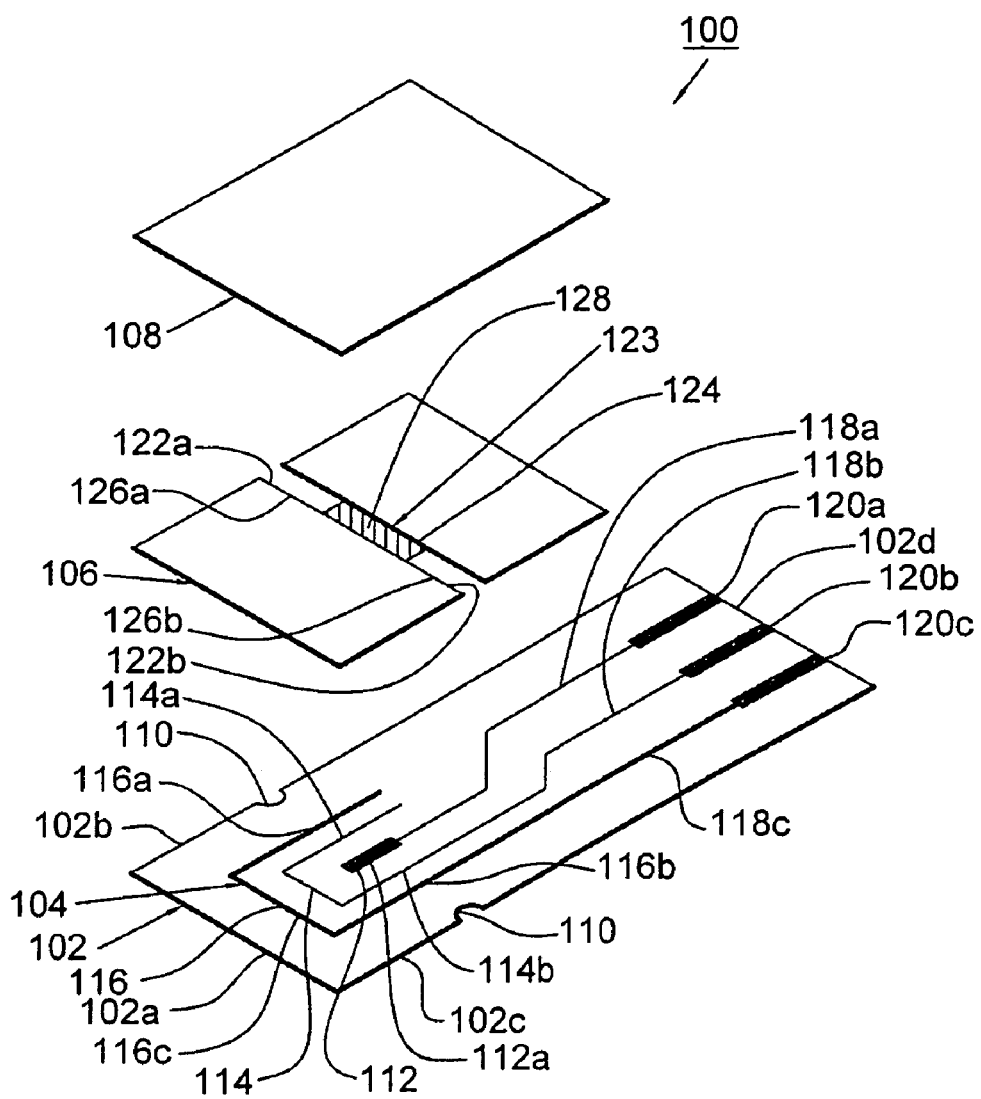
FIG. 1 is an exploded view of an electrochemical sensor according to one embodiment of the present invention.

FIG. 1 is an exploded view of an electrochemical sensor 100 according to one embodiment of the present invention. The electrochemical sensor 100 includes a first insulating layer 102, a conducting circuit 104, a spacer layer 106, and a second insulating layer 108. The first insulating layer 102 and the second insulating 108 can be made of any suitable insulating material such as a non-conducting polymer (e.g., polycarbonate, polyolefin, or polyester), or an inorganic material (e.g., metal oxide). The first insulating layer 102 has a front edge 102a, a side edge 102b, a side edge 102c, a rear edge 102d and two indentations 110 formed on the side edges 102b and 102c respectively.

The conducting circuit 104 is disposed between the first insulating layer 102 and the second insulating layer 108 and printed on the first insulating layer 102. The conducting circuit 104 includes a working electrode 112, a counter electrode 114, a timing electrode 116, conducting wires 118a, 118b, 118c, and connectors 120a, 120b, 120c. The term "working electrode" refers to an electrode on which an analyte is electrooxidized or electroreduced as redox in the presence or absence of an electron transfer agent. The term "counter electrode" refers to an electrode paired with a working electrode, through which passes an electrochemical current equal in magnitude and opposite in sign to the current passing through the working electrode.

The electrodes 112, 114 and 116 can be formed of an electrically conducting material, such as palladium, platinum, gold, silver, silver chloride, and carbon. The conducting wires 118a, 118b and 118c are coated with a dielectric material (not shown), and the connectors 120a, 120b and 120c are exposed. The working electrode 112 is electrically connected to the connector 120a through the conducting wire 118a, the counter electrode 114 is electrically connected to the connector 120b through the conducting wire 118b, and the timing electrode 116 is electrically connected to the connector 120c through the conducting wire 118c. The counter electrode 114 is formed substantially in an U shape and surrounds the working electrode 112 while the timing electrode 116 is formed substantially in an U shape and surrounds the counter electrode 114. Each of the connectors 120a, 120b and 120c has one end disposed at the rear edge 102d of the first insulating layer 102 and adapted for electrical connection to an electrochemical meter (not shown), which is capable of measuring one or more electrical parameters such as current and voltage. The parameters can be detected by amperometry and potentiometry, respectively. Details of these detecting methods can be found, for example, in U.S. Pat. No. 6,299,757, which is incorporated by reference in its entirety.

The spacer layer 106 is disposed between the first insulating layer 102 and the second insulating layer 108, and overlays the working electrode 112, the counter electrode 114 and the timing electrode 116. To facilitate connection of the connectors 120a, 120b and 120c to an electrochemical meter, the second insulating layer 108 does not cover the connectors 120a, 120b and 120c. The spacer layer 106 can be constructed from a non-conductive adhesive material, such as a pressure-sensitive adhesive or a double-sided adhesive tape. The spacer layer 106, together with the first insulating layer 102 and the second insulating layer 108, defines two adsorption ports 122a, 122b and a channel 123 between the two adsorption ports 122a and 122b. The channel 123 includes a sample section 124 and two capillaries 126a and 126b, which are respectively formed between the adsorption port 122a and the sample section 124 and between the adsorption 122b and the sample section 124. The adsorption ports 122a and 122b are aligned with the two indentations 110 of the first insulating layer 102 and positioned at the side edge 102b and the side edge 102c, respectively. When one of the adsorption ports 122a and 122b is used to draw a liquid sample, the other one will function as a vent to discharge the gas so as to facilitate delivery of the liquid sample into the sample section 124. The capillary 126a is used to receive the liquid sample drawn by the adsorption port 122a and then deliver it to the sample section 124, and the capillary 126b is used to receive the liquid sample drawn by the adsorption port 122b and then deliver it to the sample section 124. The surface on the second insulating layer 108 facing the indentations 110 provides a physical baffle to a liquid sample and facilitates delivery of the liquid sample to the capillary.

In the electrochemical sensor 100, the working electrode 112 has a conducting portion 112a, and the counter electrode 114 has a conducting portion 114a and a conducting portion 114b. The conducting portions 112a, 114a and 114b are exposed in the sample section 124. In addition, the timing electrode 116 has a conducting portion 116a and a conducting portion 116b. The conducting portion 116a and the conducting portion 116b are separated and exposed in the capillary 126a and the capillary 126b respectively. The working electrode 112 and the counter electrode 114 are positioned between the two conducting portions 116a and 116b. A test reagent 128 is formed within the sample section 124 and covers the conducting portion 112a of the working electrode 112 and the conducting portions 114a and 114b of the counter electrode 114. The test reagent 128 is an electron transfer agent that, upon reacting with an analyte in a liquid sample, transports electrons between the analyte and the working electrode 112. In this embodiment, the liquid sample can be blood or urine or other liquid to be analyzed, and the analyte can be glucose, cholesterol, uric acid, lactic acid or other biological analyte in blood, or any biological analyte in urine or in other liquid to be analyzed.

When the electrochemical sensor 100 is used to measure an analyte in a liquid sample, the connectors 120a, 120b and 120c at the rear edge 102d of the first insulating layer 102 are electrically connected to an electrochemical meter (not shown). In this embodiment, the electrochemical meter, together with the electrochemical sensor 100, forms an electrochemical sensing device for analyzing a liquid sample. Upon contacting the adsorption port 122a (or 122b), a liquid sample flows into the capillary 126a (or 126b), fills the sample section 124, and then reaches and stops at the capillary 126b (or 126a). In this embodiment, the volume of the liquid sample adsorbed into the electrochemical sensor 100 can be only several microliters, preferably, 1 to 3 microliters.

Figure 2:
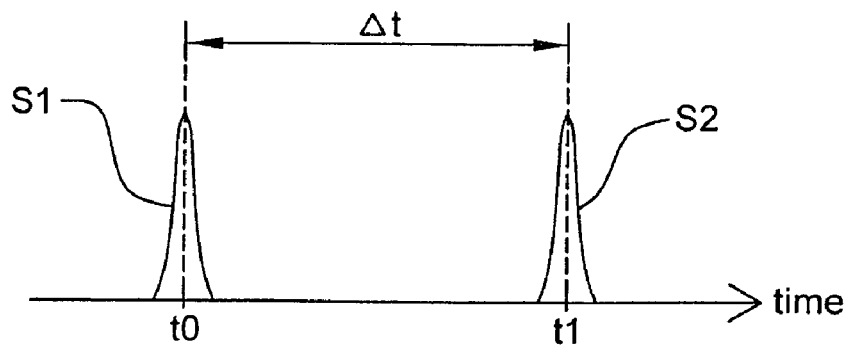
FIG. 2 shows pulses signals generated by the timing electrode of the electrochemical sensor according to embodiments of the present invention.

When the liquid sample is adsorbed into the electrochemical sensor 100 by the adsorption port 122a (or 122b), it first contacts the conducting portion 116a (or 116b) exposed in the capillary 126a (or 126b) and then contacts the conducting portion 114a (or 114b) of the counter electrode 114 in the sample section 124. When the liquid sample contacts both of the conducting portion 116a (or 116b) of the timing electrode 116 and the conducting portion 114a (or 114b) of the counter electrode 114, a first circuit is formed and a pulse signal S1 as shown in FIG. 2 is generated by the timing electrode 116 at a time t0 and transmitted to the electrochemical meter through the connector 120c (or 120b). Then, the liquid sample fills the sample section 124 and immerses both the working electrode 112 and the counter electrode 114 to form a second circuit. With a potential applied between the working electrode 112 and the counter electrode 114, an analyte-responsive signal is generated and transmitted to the electrochemical meter through the connector 120a. The analyte-responsive signal is collected by the electrochemical meter and the concentration of the analyte is calculated and obtained and then shown on the electrochemical meter. After filling the sample section 124 and reaching the capillary 126b (or 126a), the liquid sample contacts both of the conducting portion 114b (or 114a) of the counter electrode 114 and the conducting portion 116b (or 116a) of the timing electrode 116 such that a third circuit is formed and a pulse signal S2 as shown in FIG. 2 is generated by the timing electrode 116 at a time t1 and transmitted to the electrochemical meter through the connector 120c (or 120b).

In this embodiment, the electrochemical sensor 100 generates and transmits three signals, i.e. the analyte-responsive signal, the pulse signal S1 and the pulse signal S2, to the electrochemical meter. When the electrochemical meter receives the analyte-responsive signal, it calculates the concentration of the analyte according to the analyte-responsive signal and then shows a reading corresponding to the concentration of the analyte. In addition, when the electrochemical meter receives the pulse signal S1 and the pulse signal S2, it calculates the time difference $\Delta t$ between the pulse signal S1 and the pulse signal S2 as shown in FIG. 2. The time difference $\Delta t$ reflects the flow speed of the liquid sample flowing from the conducting portion 116a (or 116b) to the conducting portion 116b (or 116a). For example, the faster the liquid sample flows, the shorter the time difference $\Delta t$ is; and the slower the liquid sample flows, the longer the time difference $\Delta t$ is. In addition, the flow speed of the liquid sample is subject and proportional to the viscosity of the liquid sample itself. That is, the flow speed of the liquid sample is faster while the viscosity of the liquid sample is lower; and the flow speed is slower while the viscosity is higher. Therefore, it can be understood that the time difference $\Delta t$ is proportional to the viscosity of the liquid sample and has a specific relation with the viscosity of the liquid sample. The specific relation between the time difference $\Delta t$ and the viscosity can be created by experiments on the liquid sample flowing within the channel 123. It should be noted that viscosity is often reported in centipoises. This unit is 100 times smaller than the poise, which has the units g/cm·s; that is, grams per centimeter per second. In addition, SI unit (International System of unit) for viscosity is kg/m·s; that is, kilograms per meter per second.

In this embodiment, the electrochemical meter can calculate the viscosity of the liquid sample through the specific relation between the time difference $\Delta t$ and the viscosity. Therefore, the electrochemical meter can obtain the viscosity of the liquid sample according to the time difference $\Delta t$ and show a reading corresponding to the viscosity. The electrochemical meter according to the present invention can obtain the concentration of the analyte and the viscosity of the liquid sample within 10 seconds.

It can be understood that the conducting portion 116a and the conducting portion 116b of the timing electrode 116 shown in FIG. 1 are electrically connected to each other through a conducting portion 116c outside the channel 123. Further, the conducting portion 116a and the conducting portion 116b are separated and exposed in the channel 123, that is, the conducting portion 116a is exposed in the capillary 126a while the conducting portion 116b is exposed in the capillary 126b.

Figure 3:
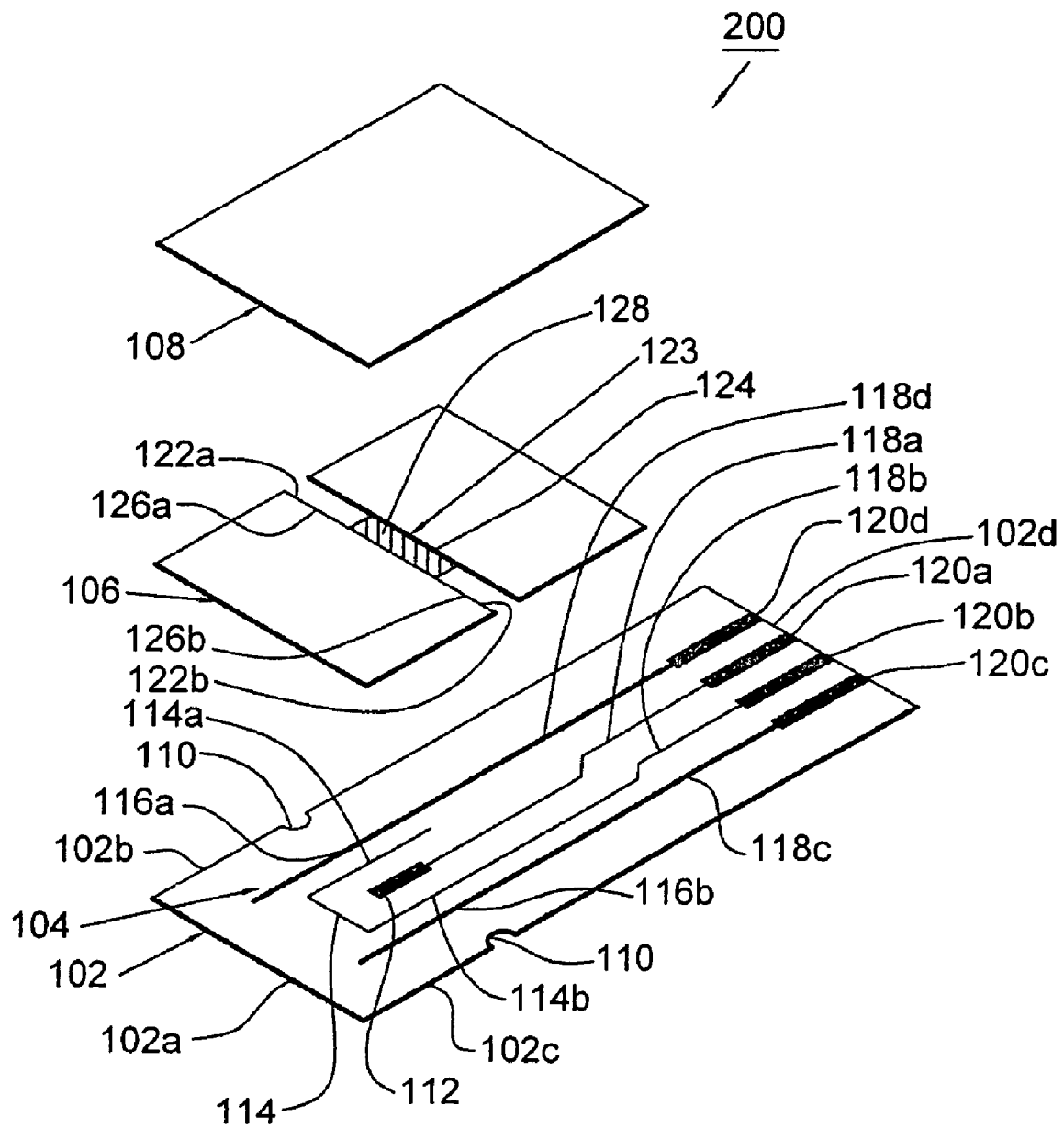
FIG. 3 is an exploded view of an electrochemical sensor according to an alternative embodiment of the present invention.

FIG. 3 is an exploded view of an electrochemical sensor 200 according to an alternative embodiment of the present invention. In FIG. 3, elements having the same functions as in the embodiment of FIG. 1 are denoted by the same numerals. The electrochemical sensor 200 is substantially the same with the electrochemical sensor 100 shown in FIG. 1 except that the conducting portion 116a and the conducting portion 116b of the timing electrode 116 are electrically separated from each other, and electrically connected to a connector 120d and the connector 120c through a conducting wire 118d and the conducting wire 118c respectively. In this alternative embodiment, when a liquid sample contacts both of the conducting portion 116a (or 116b) and the conducting portion 114a (or 114b), a pulse signal S1 as shown in FIG. 2 is generated by the conducting portion 116a (or 116b) at a time t0 and transmitted to an electrochemical meter through the connector 120d (or 120c). In addition, when the liquid sample contacts both of the conducting portion 116b (or 116a) and the conducting portion 114b (or 114a), a pulse signal S2 as shown in FIG. 2 is generated by the conducting portion 116b (or 116a) at a time t1 and transmitted to the electrochemical meter through the connector 120c (or 120d). Similarly, when the electrochemical meter receives the pulse signal S1 and the pulse signal S2, it calculates the time difference $\Delta t$ between the pulse signal S1 and the pulse signal S2 and then obtain the viscosity of the liquid sample according to the time difference $\Delta t$.

Figure 4:
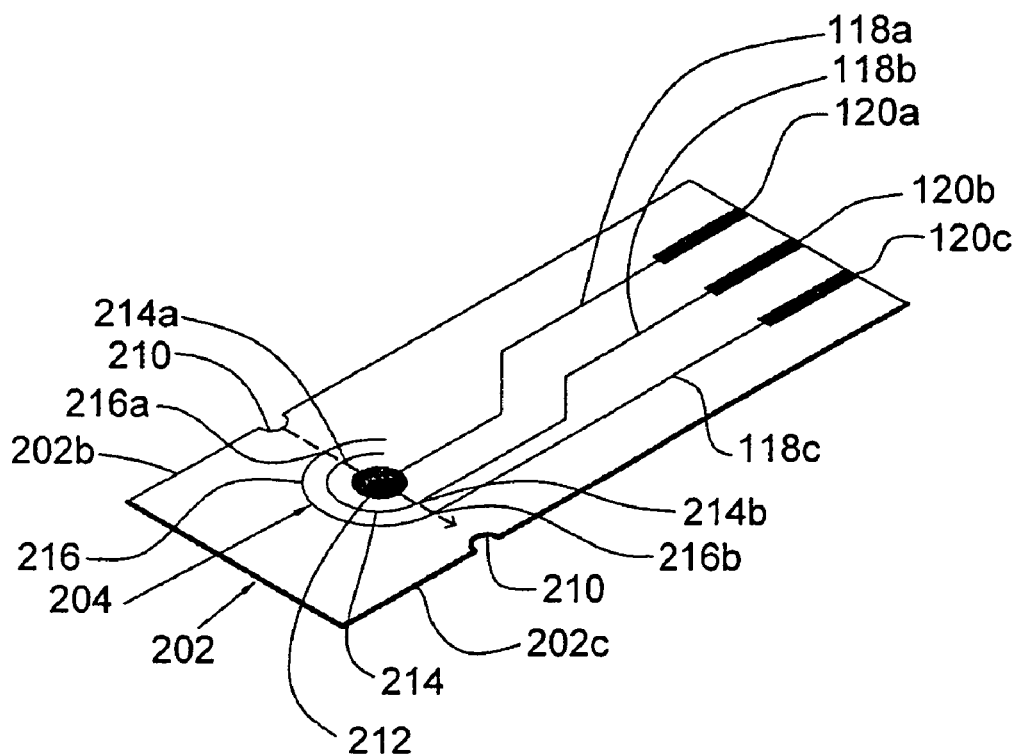
FIG. 4 is a plan view of a conducting circuit according to other embodiment of the present invention.

FIG. 4 is a plan view of a conducting circuit 204 according to other embodiment of the present invention. The conducting circuit 204 is printed on a first insulating layer 202 and includes a working electrode 212, a counter electrode 214, a timing electrode 216, conducting wires 118a, 118b, 118c, and connectors 120a, 120b, 120c. The conducting circuit 204 is substantially the same with the conducting circuit 104 shown in FIG. 1 except that the shapes of the electrodes 212, 214 and 216 are different from those of the electrodes 112, 114 and 116 shown in FIG. 1. The counter electrode 214 surrounds the working electrode 212 while the timing electrode 216 surrounds the counter electrode 214. A retest agent (not shown) reacting with an analyte is formed on parts of the working electrode 212 and the counter electrode 214.

When an electrochemical sensor having the conducting circuit 204 is used to measure an analyte in a liquid sample, the liquid sample can be adsorbed into the electrochemical sensor from the indentation 210 at the side edge 202b and then flows, in a direction as the dotted arrow shown in FIG. 4, through a conducting portion 216a of the timing electrode 216, a conducting portion 214a of the counter electrode 214, the working electrode 212, a conducting portion 214b of the counter electrode 214, and finally reaches a conducting portion 216b of the timing electrode 216. Alternatively, the liquid sample can also be adsorbed into the electrochemical sensor from the indentation 210 at the side 202c and then flows, in a direction opposite to the dotted arrow shown in FIG. 4, toward the conducting portion 216a of the timing electrode 216. Similar to the conducting circuit 104 shown in FIG. 1, the timing electrode 216 generates a pulse signal S1 at a time t0 as shown in FIG. 2 when the liquid sample first contacts both of the conducting portion 216a (or 216b) of the timing electrode 216 and the conducting portion 214a (or 214b) of the counter electrode 214. Afterward, the timing electrode 216 generates a pulse signal S2 at a time t1 as shown in FIG. 2 when the liquid sample then contacts both of the conducting portion 214b (or 214a) of the counter electrode 214 and the conducting portion 216b (or 216a) of the timing electrode 216. Similarly, an electrochemical meter (not shown) can calculate the time difference Δt between the pulse signal S2 and the pulse signal S1, obtain the viscosity of the liquid sample according to the time difference Δt, and then show a reading corresponding to the viscosity.

In addition, when the liquid sample contacts both the working electrode 212 and the counter electrode 214, the working electrode 212 generates an analyte-responsive signal and transmits it to the electrochemical meter through the connector 120a. The electrochemical meter calculates and obtains the concentration of an analyte in the liquid sample according to the analyte-responsive signal and then shows a reading corresponding to the concentration of the analyte.

Figure 5:
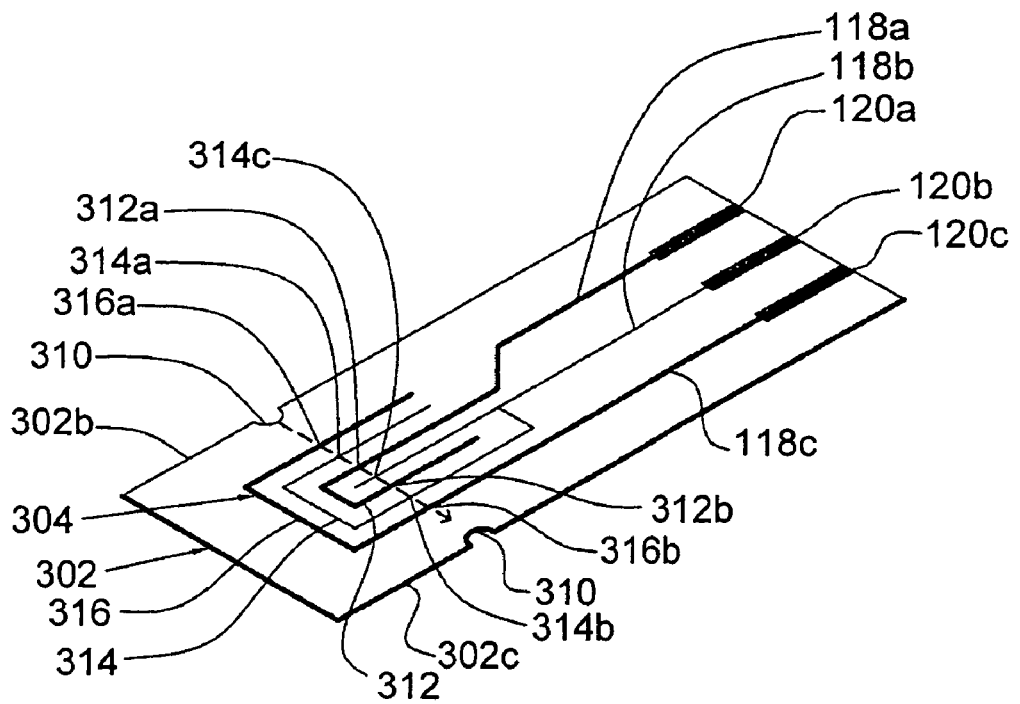
FIG. 5 is a plan view of a conducting circuit according to other embodiment of the present invention.

FIG. 5 is a plan view of a conducting circuit 304 according to other embodiment of the present invention. The conducting circuit 304 is printed on a first insulating layer 302 and includes a working electrode 312, a counter electrode 314, a timing electrode 316, conducting wires 118a, 118b, 118c, and connectors 120a, 120b, 120c. The conducting circuit 304 is substantially the same with the conducting circuit 104 shown in FIG. 1 except that the shapes of the electrodes 312 and 314 are different from those of the electrodes 112 and 114 shown in FIG. 1. The working electrode 312 is formed substantially in an U shape and surrounds a conduction portion 314c of the counter electrode 314. The counter electrode 314 surrounds the working electrode 312 while the timing electrode 316 surrounds the counter electrode 314. A test reagent (not shown) reacting with an analyte is also formed on parts of the working electrode 312 and the counter electrode 314.

When an electrochemical sensor having the conducting circuit 304 is used to measure an analyte in a liquid sample, the liquid sample can be adsorbed into the electrochemical sensor from the indentation 310 at the side edge 302b and then flows, in a direction as the dotted arrow shown in FIG. 5, through a conducting portion 316a of the timing electrode 316, a conducting portion 314a of the counter electrode 314, a conducting portion 312a of the working electrode 312, the conducting portion 314c of the counter electrode 314, a conducting portion 312b of the working electrode 312, a conducting portion 314b of the counter electrode 314, and finally reaches a conducting portion 316b of the timing electrode 316. Alternatively, the liquid sample can also be adsorbed into the electrochemical sensor from the indentation 310 at the side 302c and then flows, in a direction opposite to the dotted arrow shown in FIG. 5, toward the conducting portion 316a of the timing electrode 316. Similar to the conducting circuit 104 shown in FIG. 1, the timing electrode 316 generates a pulse signal S1 at a time t0 as shown in FIG. 2 when the liquid sample first contacts both of the conducting portion 316a (or 316b) of the timing electrode 316 and the conducting portion 314a (or 314b) of the counter electrode 314. Afterward, the timing electrode 316 generates a pulse signal S2 at a time t1 as shown in FIG. 2 when the liquid sample then contacts both of the conducting portion 314b (or 314a) of the counter electrode 314 and the conducting portion 316b (or 316a) of the timing electrode 316. Similarly, an electrochemical meter (not shown) can calculate the time difference Δt between the pulse signal S2 and the pulse signal S1, obtain the viscosity of the liquid sample according to the time difference Δt, and then show a reading corresponding to the viscosity.

In addition, when the liquid sample contacts both the working electrode 312 and the counter electrode 314, the working electrode 312 generates an analyte-responsive signal and transmits it to the electrochemical meter through the connector 120a. The electrochemical meter calculates and obtains the concentration of an analyte in the liquid sample according to the analyte-responsive signal and then shows a reading corresponding to the concentration of the analyte.

It should be noted that the electrochemical sensors described above have two adsorption ports, one of which is used to draw a liquid sample while the other one functions as a vent, disposed at two side edges thereof. However, according to the electrochemical sensors of the present invention, the adsorption port and the vent are not limited to be disposed at two side edges respectively and could be changed with other different features. An electrochemical sensor having an adsorption port disposed at its front edge will be described below.

Figure 6:
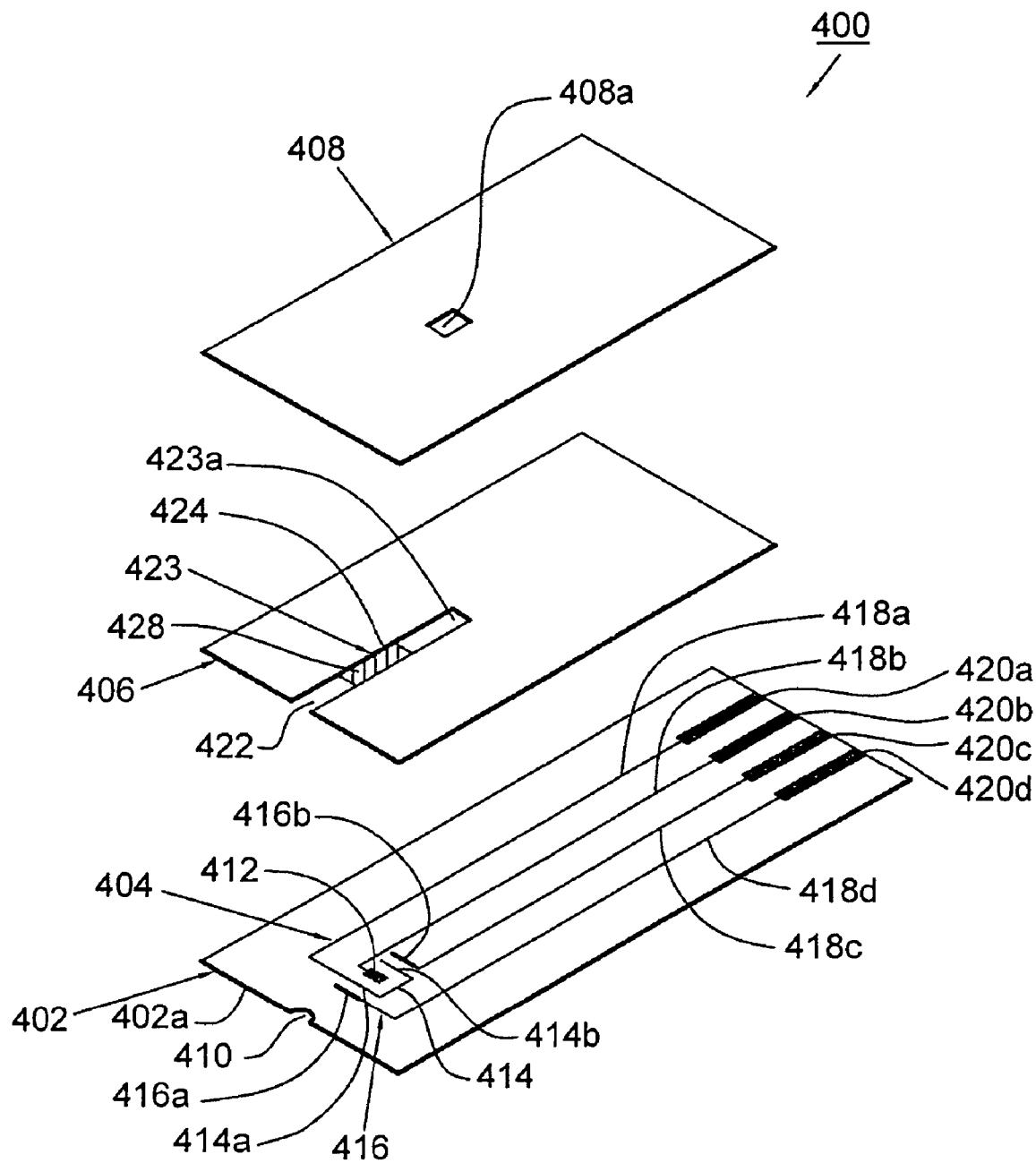
FIG. 6 is an exploded view of an electrochemical sensor according to other embodiment of the present invention.

FIG. 6 is an exploded view of an electrochemical sensor 400 according to other embodiment of the present invention. The electrochemical sensor 400 includes a first insulating layer 402, a conducting circuit 404, a spacer layer 406, and a second insulating layer 408. The first insulating layer 402 has an indentation 410 formed on a front side 410a. The conducting circuit 404 is disposed between the first insulating layer 402 and the second insulating layer 408 and printed on the first insulating layer 402. The conducting circuit 404 includes a working electrode 412, a counter electrode 414, a timing electrode 416 including a conducting portion 416a and a conducting portion 416b, conducting wires 418a, 418b, 418c, 418d and connectors 420a, 420b, 420c, 420d.

The spacer layer 406 is disposed between the first insulating layer 402 and the second insulating layer 408, and overlays the working electrode 412, the counter electrode 414 and the timing electrode 416. The connectors 420a, 420b, 420c and 420d are exposed from the spacer layer 406 and the second insulating layer 408 so as to facilitate connection of the connectors 420a, 420b, 420c and 420d to an electrochemical meter.

In addition, the spacer layer 406, together with the first insulating layer 402 and the second insulating layer 408, defines an adsorption port 422 and a channel 423 extended from the adsorption port 422. The channel 423 includes an end section 423a opposite to the adsorption port 422, and a sample section 424 formed between the adsorption port 422 and the end section 423a. The adsorption port 422 is aligned with the indentation 410 of the first insulating layer 402 and positioned at the front edge 402a. The second insulating layer 408 has a vent 408a formed thereon and above the end section 423a of the channel 423.

When the adsorption port 422 draws a liquid sample, the vent 408a discharges the gas so as to facilitate delivery of the liquid sample into the sample section 424. The surface on the second insulating layer 408 facing the indentations 410 provides a physical baffle to a liquid sample and facilitates delivery of the liquid sample to the channel 423.

In the electrochemical sensor 400, the counter electrode 414 has a conducting portion 414a and a conducting portion 414b. The working electrode 412, the conducting portions 414a and 414b of the counter electrode 414 are exposed in the sample section 424 of the channel 423. The conducting portion 416a and the conducting portion 416b of the timing electrode 416 are also exposed in the channel 423. A test reagent 428 is formed within the sample section 424 and covers the working electrode 412 and the conducting portions 114a and 114b of the counter electrode 114.

When the electrochemical sensor 400 is used to measure an analyte in a liquid sample, the liquid sample can be adsorbed into the electrochemical sensor 400 from the indentation 410 at the front edge 402a and then flows through the conducting portion 416a of the timing electrode 416, the conducting portion 414a of the counter electrode 414, the working electrode 412, the conducting portion 414b of the counter electrode 414, and finally reaches the conducting portion 416b of the timing electrode 416. In this embodiment, when the liquid sample contacts both of the conducting portion 416a and the conducting portion 414a, a pulse signal S1 as shown in FIG. 2 is generated by the conducting portion 416a at a time t0 and transmitted to an electrochemical meter through the connector 420d. In addition, when the liquid sample contacts both of the conducting portion 416b and the conducting portion 414b, a pulse signal S2 as shown in FIG. 2 is generated by the conducting portion 416b at a time t1 and transmitted to the electrochemical meter through the connector 420c. Similarly, when the electrochemical meter receives the pulse signal S1 and the pulse signal S2, it calculates the time difference $\Delta t$ between the pulse signal S1 and the pulse signal S2 and then obtain the viscosity of the liquid sample according to the time difference $\Delta t$.

In addition, when the liquid sample contacts both the working electrode 412 and the counter electrode 414, the working electrode 412 generates an analyte-responsive signal and transmits it to the electrochemical meter through the connector 420b. The electrochemical meter calculates and obtains the concentration of an analyte in the liquid sample according to the analyte-responsive signal and then shows a reading corresponding to the concentration of the analyte.

In the electrochemical sensing device of the present invention, the electrochemical meter according to the above-mentioned embodiments can utilize the time difference $\Delta t$ to calibrate an concentration value of an analyte in a liquid sample. For example, if the liquid sample described in the above-mentioned embodiment is a blood sample and the concentration of the analyte to be measured is blood glucose, the time difference $\Delta t$ also can be utilized to obtain hematocrit (HCT) in the blood sample, wherein the hematocrit is the percentage of the volume of the blood sample occupied by red blood cells. In the prior art, it is known that a higher hematocrit (higher than 60%) or a lower hematocrit (lower than 30%) in a blood sample would cause deviation in a blood glucose value measured by an electrochemical sensing device. More specifically, a higher hematocrit in a blood sample may cause the electrochemical sensing device to obtain a lower blood glucose value while a lower hematocrit in the blood sample may cause the electrochemical sensing device to obtain a higher blood glucose value. Therefore, the blood glucose value obtained by an electrochemical sensing device is usually not accurate due to different hematocrit (HCT) in the blood sample and needs to be calibrated. In the prior art, the blood glucose value obtained by a conventional electrochemical sensing device can be calibrated by being multiplied by a calibrating factor, wherein the calibrating factor can be obtained by collecting and analyzing a large number of experimental results. However, the calibrating step can only be done by a user and not by the electrochemical sensing device itself. The electrochemical meter according to the above-mentioned embodiments can obtain the hematocrit according to the difference $\Delta t$, wherein a relation between the difference $\Delta t$ and the hematocrit can be created by clinical experiments. In addition, the electrochemical meter according to the above-mentioned embodiments has a lookup table stored therein, which contains a plurality of calibrating factors corresponding to a plurality of different hematocrits. In the above-mentioned embodiments, the electrochemical meter can obtain a hematocrit according to the difference $\Delta t$, look up a calibrating factor corresponding to the hematocrit in the lookup table, and then calibrate the obtained blood glucose value by the calibrating factor. Accordingly, the electrochemical meter according to the present invention can not only obtain viscosity of a liquid sample according to the time difference $\Delta t$ but also calibrate a concentration value of an analyte in the liquid sample according to the time difference $\Delta t$ such that an concentration value obtained by an electrochemical sensing device can be more accurate.

In the above-mentioned embodiments, the electrochemical sensors 100, 200, 400 are capable of measuring viscosity of a liquid sample within several seconds. Also, the electrochemical sensors 100, 200, 400 can only take a liquid sample of several microliters, which is far less than the sample volume conventional viscometers require, to obtain the viscosity of the liquid sample. In addition, the electrochemical meter of the present invention can use the electrochemical sensor 100, 200, or 400 to calibrate a concentration value of an analyte in the liquid sample. Therefore, the electrochemical sensor and meter of the present invention have at least above-mentioned advantages over the prior art.

The present invention also provides a method for analyzing a liquid sample, wherein the method is applied to an electrochemical sensing device having an electrochemical meter and an electrochemical sensor. The method of the present invention comprises the following steps and is described below by referring to FIGS. 1 and 2. Firstly, a first conducting portion 116a and a second conducting portion 116b are disposed in an electrochemical sensor 100. Secondly, a first pulse signal S1 is generated and transmitted to the electrochemical meter (not shown) when a liquid sample flows through the capillaries 126a and contacts the first conducting portion 116a, and a second pulse signal S2 is generated and transmitted to the electrochemical meter when the liquid sample flows through the capillaries 126b and contacts the second conducting portion 126b. Then, a time difference $\Delta t$ between the first pulse signal S1 and the second pulse signal S2 is calculated by the electrochemical meter. After the time difference $\Delta t$ is calculated, the electrochemical meter can obtain viscosity of the liquid sample according to the time difference $\Delta t$ and then show a reading corresponding to the viscosity of the liquid sample. In addition, after the time difference $\Delta t$ is calculated, the electrochemical meter can also calculate and obtain concentration of an analyte in the liquid sample according to an analyte-responsive signal, calibrate the obtained concentration of the analyte according to the time difference $\Delta t$ and then show a reading corresponding to the calibrated concentration of the analyte.

Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. An electrochemical sensing device for analyzing a liquid sample, comprising:

a U-shaped timing electrode having a first conducting portion electrically connected to a second conducting portion, wherein the first and second conducting portions are substantially parallel to each other;

a counter electrode enclosed by the timing electrode, the counter electrode having a U-shaped portion enclosing and electrically connected to a third conducting portion, the U-shaped portion having a first conducting portion electrically connected to a second conducting portion, wherein the first, second, and third conducting portions of the counter electrode are substantially parallel to each other;

a U-shaped working electrode enclosed by the U-shaped portion of the counter electrode, the U-shaped working electrode enclosing the third conducting portion of the counter electrode and having a first conducting portion electrically connected to a second conducting portion, wherein the first and second conducting portions of the U-shaped working electrode are substantially parallel to each other;

a test reagent formed on both the working and counter electrodes to react with an analyte in the liquid sample; and an electrochemical meter electrically connected to the timing electrode, the counter electrode, and the U-shaped working electrode, wherein a first pulse signal is generated when the liquid sample contacts both the first conducting portion of the counter electrode and the first conducting portion of the timing electrode;

wherein a second pulse signal different from the first pulse signal is generated when the liquid sample contacts both the second conducting portion of the counter electrode and the second conducting portion of the timing electrode;

wherein the electrochemical meter is programmed to calculate the viscosity of the liquid sample based on both the first and second pulse signals; and wherein the electrochemical meter is programmed to calculate a concentration of the analyte according to an analyte-responsive signal transmitted to the electrochemical meter when the liquid sample contacts both the U-shaped working electrode and counter electrode.

2. The electrochemical sensing device as claimed in claim 1 wherein said liquid sample is one of blood and urine, and said analyte is selected from the group consisting of glucose, cholesterol, uric acid and lactic acid.

3. The electrochemical sensing device as claimed in claim 1, wherein said timing electrode, said counter electrode and said working electrode are disposed on an insulating layer.

4. The electrochemical sensing device as claimed in claim 1, wherein the viscosity of the liquid sample is obtained by calculating a time difference between the first and second pulse signals.

* * * * *